(12) United States Patent
Belpasso

(10) Patent No.: US 10,709,216 B2
(45) Date of Patent: Jul. 14, 2020

(54) PHILSRING HEALTH AID

(71) Applicant: Philip Ralph Belpasso, Fair Lawn, NJ (US)

(72) Inventor: Philip Ralph Belpasso, Fair Lawn, NJ (US)

(*) Notice: Subject to any disclaimer, the term of this patent is extended or adjusted under 35 U.S.C. 154(b) by 0 days.

(21) Appl. No.: 16/295,732

(22) Filed: Mar. 7, 2019

(65) Prior Publication Data
US 2019/0254392 A1 Aug. 22, 2019

(51) Int. Cl.
A44C 9/00 (2006.01)
A61M 21/00 (2006.01)
A44C 25/00 (2006.01)

(52) U.S. Cl.
CPC .......... A44C 9/0053 (2013.01); A44C 25/005 (2013.01); A61M 2021/0044 (2013.01)

(58) Field of Classification Search
CPC ....... A44C 5/0023; A44C 5/0092; A44C 9/00; A44C 9/0053; A44C 9/02; B21D 53/00
USPC .............. 63/15, 15.45, 15.5; D11/26, 3
See application file for complete search history.

(56) References Cited

U.S. PATENT DOCUMENTS

| 1,465,682 A | * | 8/1923 | Pollack | B21D 53/44 |
| | | | | 29/8 |
| D426,170 S | * | 6/2000 | Leighton | D11/3 |
| 2011/0132036 A1 | * | 6/2011 | Meltzer | A44C 17/0233 |
| | | | | 63/29.1 |

* cited by examiner

Primary Examiner — Jack W Lavinder

(57) ABSTRACT

A jewelry product the form of an annular copper ring having a receiving passage through-hole. The annular copper ring shank includes a through-bore extending from an outer circumferential surface to an inner circumferential surface in a radial direction of the copper ring. The annular copper ring shank has a flattened area on the outer circumferential surface to facilitate engagement with an inner surface of the head of an ornament. The ornament includes a threaded shaft extending from the inner surface of the head. The threaded shaft engages the through-bore and terminates at a flanged end to make a secured connection between the screw and the inner circumferential surface of the ring shank. The flanged end is flush with the inner circumferential surface of the ring shank to provide a continuous, smooth transition between the inner circumferential surface and the flange.

1 Claim, 5 Drawing Sheets

PHILSRING HEALTH AID

HISTORY OF DESIGN

The Phillips-head shape has been available since the nineteen thirties and defined by U.S. Pat. No. 2,046,343, H. F. Phillips filed 3, 1934. Therefore, this Phillips Ring is a tribute to that patent as being an important technological advance.

DETAILED DESCRIPTION

Figure 1:
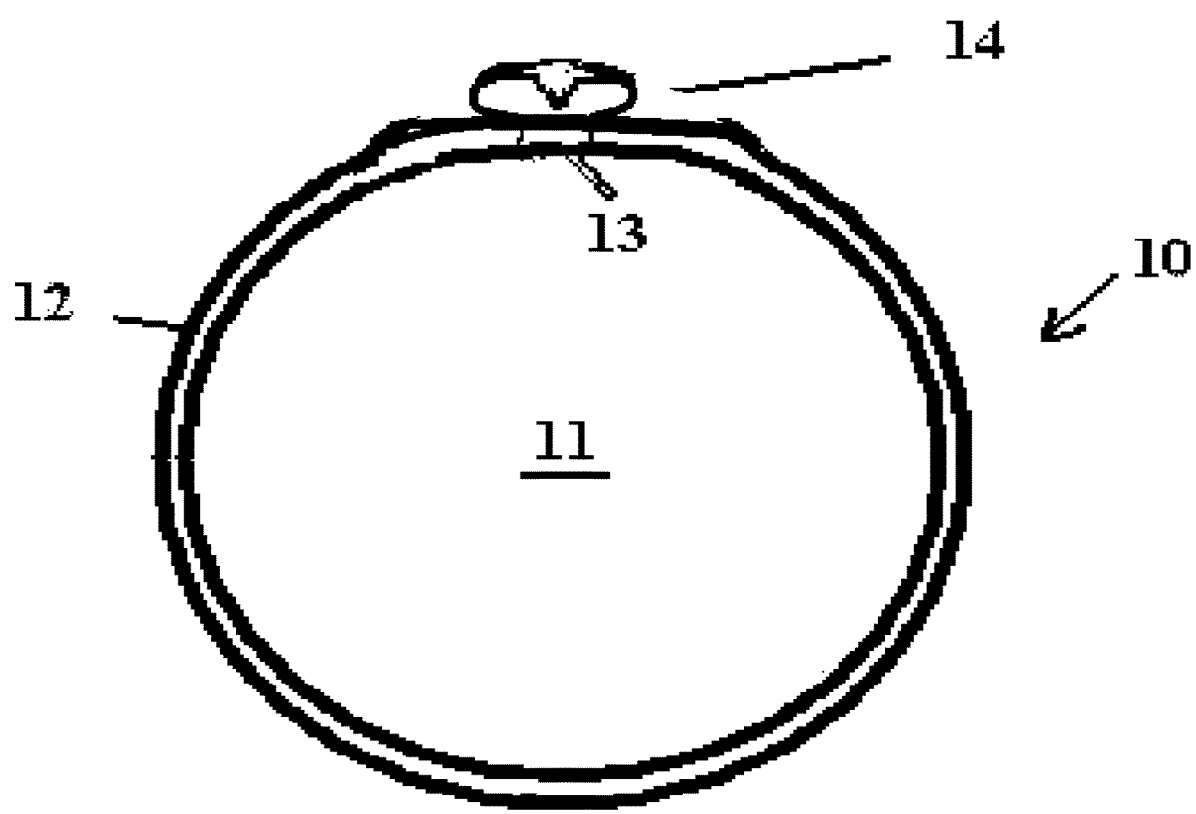
FIG. 1 is a top view of a first embodiment of the present invention, including a base annular ring shank member with the ornamental Phillips screw mounted on it.
Figure 2:
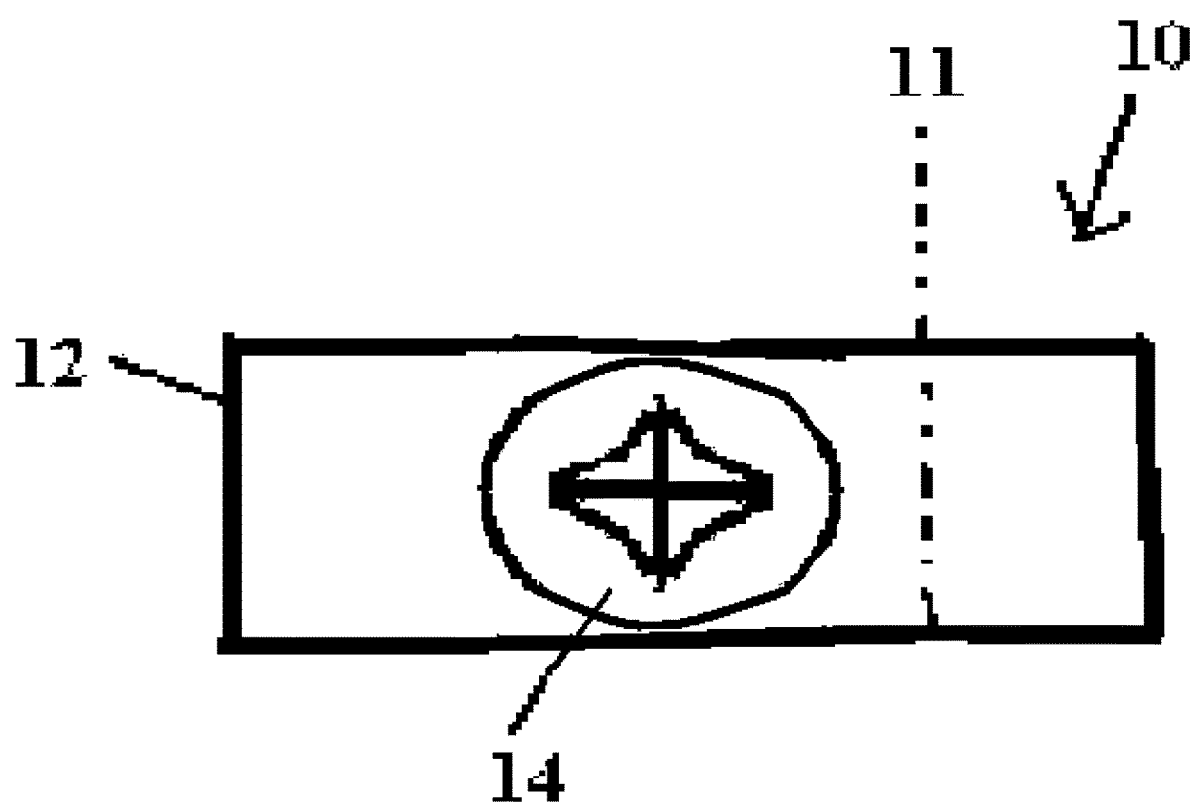
FIG. 2 is a front view of FIG. 1.
Figure 3:
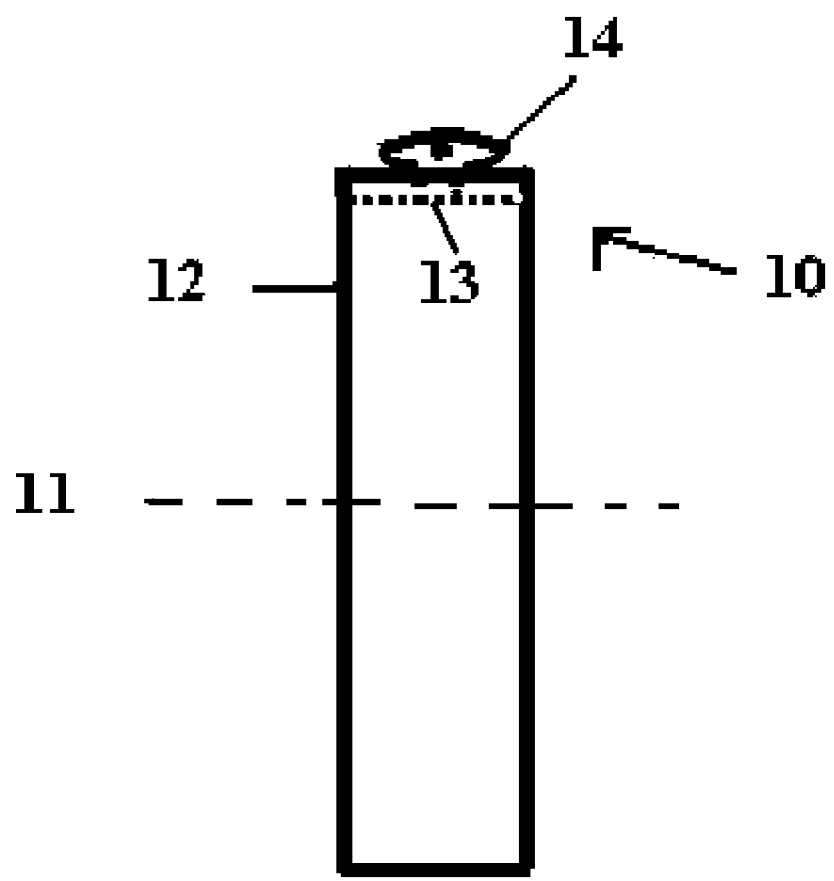
FIG. 3 side view of FIG. 1 and FIG. 2.

Reference is made to a first embodiment of the present invention and is illustrated in FIGS. 1-3.

Figure 4:
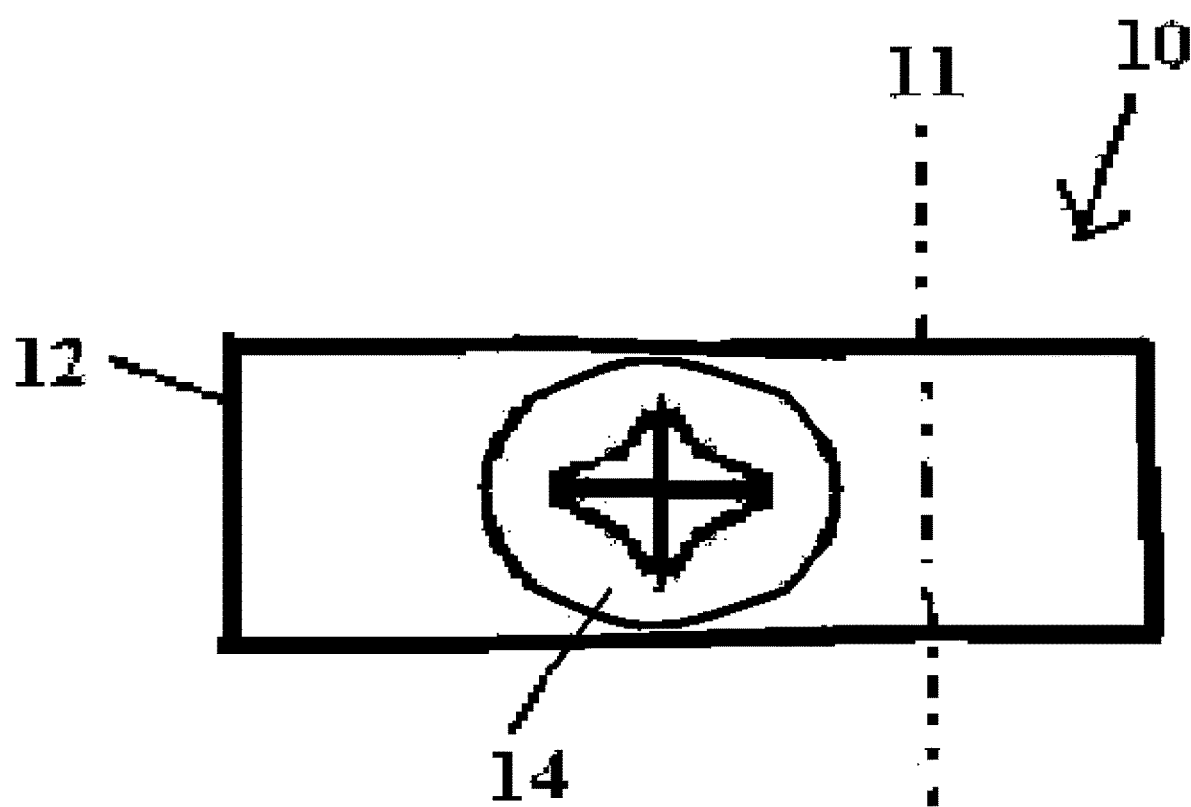
FIG. 4 is a front view of the one embodiment of the screwed in " the Phillips head & quot; member.
Figure 5:
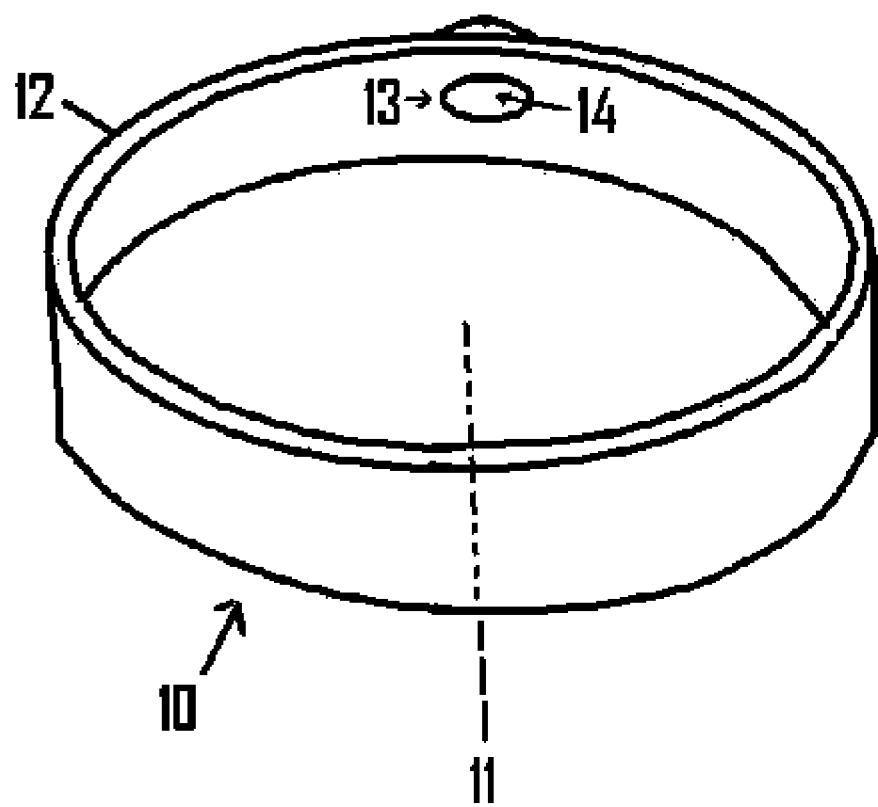
FIG. 5 is a perspective view illustrated in FIG. 4 with the real screw member screwed into the ring member.

This jewelry product is comprised of an annular copper ring (10) having a receiving passage through-hole (11) to be engaged with the user. The annular copper ring shank (12) includes a through-bore (13) extending from an outer circumferential surface to an inner circumferential surface in a radial direction of the copper ring, i.e., the radial direction is the direction along a radial line extending from the center of the passage through-hole (11). The annular copper ring shank (12) has a flattened area on the outer circumferential surface to facilitate engagement with an inner surface of the head (14) of an ornament, which is a Phillips head screw. The ornament includes a threaded shaft Application/Control extending from the inner surface of the head (14). The threaded shaft engages the through-bore (13) and terminates at a flanged end to make a secured connection between the screw and the inner circumferential surface of the ring shank. The flanged end (at 13 in FIG. 1) is flush with the inner circumferential surface of the ring shank to provide a continuous, smooth transition between the inner circumferential surface and the flange. The Phillips head screw (14) is connected via the through-bore (13) with its top head facing outwardly from the outer circumferential surface of the ring shank (12). Reference is now made to a second embodiment of the present invention. FIG. 4 is a photo of the front view of this second embodiment. FIG. 5 is a photo of the rear view of this second embodiment.

I claim:

1. An article of jewelry consisting of
an annular copper ring shank forming a through-hole passage, said annular copper ring shank having an outer circumferential surface, an inner circumferential surface, and a width defined in a radial direction of said annular copper ring shank between said outer and inner circumferential surfaces, said width being larger at a portion of said annular copper ring shank having:
a.) a through-bore extending in said radial direction through said annular copper ring shank from said outer circumferential surface of said annular copper ring shank to said inner circumferential surface of said annular copper ring shank
b.) a planar surface on said outer circumferential surface; and,
an ornament having a head with an outer surface including a groove formed therein and an inner surface with a copper threaded shaft extending therefrom, said threaded shaft extending into said through-bore terminating at a flanged end at said inner circumferential surface of said annular copper ring shank while a portion of said head inner surface is engaged with said planar surface on said outer circumferential surface of said annular copper ring shank, said flanged end being flush with said inner circumferential surface of said annular copper ring shank to provide a continuous, smooth transition between said inner circumferential surface of said annular copper ring shank and said flange.

* * * * *